(12) United States Patent
Thakur

(10) Patent No.: US 8,017,694 B2
(45) Date of Patent: Sep. 13, 2011

(54) EFFICIENT PROCESS OF VULCANIZATION OF NONCONJUGATED CONDUCTIVE POLYMERS INCLUDING RUBBERS

(76) Inventor: Mrinal Thakur, Auburn, AL (US)

(*) Notice: Subject to any disclaimer, the term of this patent is extended or adjusted under 35 U.S.C. 154(b) by 0 days.

(21) Appl. No.: 12/244,054

(22) Filed: Oct. 2, 2008

(65) Prior Publication Data
US 2009/0020731 A1    Jan. 22, 2009

Related U.S. Application Data

(63) Continuation-in-part of application No. 11/046,173, filed on Jan. 28, 2005, now Pat. No. 7,641,977.

(60) Provisional application No. 60/539,803, filed on Jan. 28, 2004.

(51) Int. Cl.
*C08C 19/28* (2006.01)

(52) U.S. Cl. ............... 525/332.5; 525/331.7; 525/326.1; 525/332.6; 525/331.8; 525/355; 252/500; 252/511

(58) Field of Classification Search ............... 525/332.5, 525/331.7, 326.1, 332.6, 331.8, 355; 252/500, 252/511
See application file for complete search history.

(56) References Cited

U.S. PATENT DOCUMENTS 6,565,453 B2 * 5/2003 Maruoka ...................... 473/357

OTHER PUBLICATIONS

Thakur, "A class of Conducting Polymers having Nonconjugated Backbones", Macromolecules, 21, 661-664 (1988).*

* cited by examiner

*Primary Examiner* — Ling-Siu Choi
(74) *Attorney, Agent, or Firm* — Thomas, Kayden, Horstemeyer & Risley, LLP.

(57) ABSTRACT

Nonconjugated conductive polymers, which are all polymers that have a ratio of double bonds to total bonds of less than ½ are doped with iodine to produce compositions with unexpected characteristics in this invention. The mechanical and elastomeric properties of a nonconjugated polymer can be enhanced by doping the polymer with an electron acceptor such as iodine, in order to cure the polymer. Among the nonconjugated polymers are the cis-1,4-polyisoprene, cis-1,4 polybutadiene, styrene-butadiene copolymers (SBR), ethylene-propylene-diene monomer and poly (β-pinene). A heated mixture of iodine and sulfur produces a faster rate of vulcanization of rubber than using sulfur alone.

12 Claims, No Drawings

EFFICIENT PROCESS OF VULCANIZATION OF NONCONJUGATED CONDUCTIVE POLYMERS INCLUDING RUBBERS

CROSS-REFERENCE TO RELATED APPLICATIONS

This application is a continuation-in-part of U.S. non provisional application entitled, "NOVEL APPLICATIONS OF NONCONJUGATED CONDUCTIVE POLYMERS," having Ser. No. 11/046,173, filed Jan. 28, 2005, now U.S. Pat. No. 7,641,977 which is entirely incorporated herein by reference which in turn claims priority to U.S. Provisional Application entitled, "NOVEL APPLICATIONS OF NON-CONJUGATED CONDUCTIVE POLYMERS," having Ser. No. 60/539,803, filed Jan. 28, 2004 all of which is entirely incorporated herein by reference.

BACKGROUND OF THE INVENTION

Field of the Invention

This invention relates to a new efficient process of vulcanization of nonconjugated conductive polymers including rubbers. Nonconjugated conductive polymers have a least one double bond which is repeated in a ratio of double bond to total bonds that is a lower fraction than ½. It has been found that these polymers can be vulcanized more efficiently and have superior mechanical properties using the new process.

SUMMARY OF THE INVENTION

Polymers have a wide range of applications. In this disclosure, a new efficient process is described for vulcanizing nonconjugated conductive polymers which results in them having superior mechanical properties. Conjugated polymers have a repeat with one double bond followed by a single bond, which is followed by another double bond and a single bond. Thus, there is a ratio of double bonds to total bonds, ½. Nonconjugated conductive polymers include polymers with at least one double bond in the repeat. Nonconjugated polymers include all of those polymers that have a ratio of double bond to total bonds, that is a lower fraction than ½. It includes polymers where there is only one double bond in each repeat. It will be recognized that there can be two or more double bonds in the repeat if the ratio of double bonds and total bonds is lower than "½." Upon doping, a charge-transfer takes place between the isolated double bond of the polymer and the dopant. For example, in the case of iodine doping, an electron is transferred from the double bond to iodine, thus, creating a radical cation consisting of a hole or positive charge and a radical at the double bond site. This hole then participates in the electrical conductivity through intersite hopping. The conductivity increases by about 100 billion times upon doping.

Examples of nonconjugated conductive polymers include natural rubber, styrene-butadiene rubber, poly(β-pinene) and other similar polymers. It has been found that by doping these nonconjugated polymers with an electron acceptor, such as iodine, or a mixture of iodine and sulfur and subsequently heating leads to more efficient vulcanization and unusual and superior materials and properties as explained infra.

DETAILED DESCRIPTION OF THE PREFERRED EMBODIMENTS

Enhanced Mechanical and Elastomeric Properties

Polymers have a wide range of mechanical and structural applications. Depending on applications, the strength, flexibility, elastic deformability and easy processing are used in almost everywhere including, home appliances, in construction, automotive, industrial, aerospace and many other applications. In the present invention, improved mechanical properties of iodine doped nonconjugated polymers are discussed.

The nonconjugated polymers that have been investigated include elastomers such as cis-1,4-polyisoprene, cis-1,4 polybutadiene, styrene-butadiene copolymers (SBR) and ethylene-propylene-diene monomer (EPDM). The nonconjugated polymers have at least one isolated double bond in the repeat. Doping of the polymer leads to transfer of an electron from the isolated double bond to the dopant, creating a hole or positive charge at the double-bond site. The hole thus created leads to electrical conduction via intersite hopping as a voltage is applied.

The nonconjugated polymers including natural rubber, polybutadiene, EPDM and SBR are commercially important for a wide range of applications. In automotive tires alone many billion pounds of these polymers are used per year. Consequently, an improvement of mechanical properties and/or cost reduction can have substantial economic impact in the long term. The results disclosed here show that the mechanical properties of natural rubber, polybutadiene and SBR are substantially enhanced upon doping with chemicals such as iodine prior to curing the polymer. These enhancements include increase of tensile strength, elastic modulus and resilience of the materials. Such characteristics are important for applications in tires and many other rubber products.

Process of Vulcanization

As it is well known, raw natural rubber has little application since it is tacky, with little resilience. Vulcanization of natural rubber provides the effective elastomeric properties for applications such as in tires. The vulcanization using sulfur leads to cross-linking and enhancement of mechanical properties of rubber. Besides vulcanization, additives such as carbon black are needed to reduce static electricity and increase strength.

It has been found that doping of a nonconjugated polymer with an electron acceptors such as iodine, results in the curing or vulcanization of nonconjugated polymers, such as natural rubber (cis-1,4-polyisoprene), cis-1,4 polybutadiene, styrene-butadiene copolymers, ethylene-propylene-diene monomer and poly(β-pinene). In this process the polymer in the form of a latex is cast on a surface so that the water is allowed to evaporate. The latex is then doped with iodine and allowed to cure. A controlled amount of iodine can be used so that there is no residual unreacted iodine that needs to be removed from the polymer. If the amount of iodine is not controlled, then a solvent such as hexane can be used to remove the residual unreacted iodine. Fillers such as carbon black can be incorporated in the curing. It has been found that curing or vulcanizing these nonconjugated polymers with iodine results in a rubber that is mechanically much stronger and has significantly enhanced elastomeric properties even without using fillers such as carbon black. Sulfur can be combined with the iodine in the process, if desired. Heat will speed the vulcanization process with iodine or with a combination of iodine and sulfur.

In addition, vulcanization through iodine doping has other important applications. Waste/scrap tires are known to attract insects such as mosquitoes for breeding. Various types of mosquitoes leading to a number of dangerous diseases are found on scrap tires. The scrap tire piles need to be treated with specific insecticides to reduce these health problems. However, treatment with insecticides often is not hundred percent successful since the insecticides may not reach the depth of the piles where the mosquitoes rest. This problem can be solved by making the tires made in a different way such that the tires repel mosquitoes. Iodine as a dopant or vulcanization agent in tires acts as an insecticide. The tires made by iodine doping or using a mixture of iodine and sulfur overcomes the problem of insect-breeding. Iodine doping may lead to other advantages in tire recycling.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

Example 1

A natural rubber (cis-1,4 polyisoprene) sample in the form of latex was obtained from Firestone Inc. Solid specimens of specific sizes and shapes were prepared by casting of the latex on a Teflon-coated aluminum substrate and by evaporation of the water. The samples were doped with iodine at different molar concentrations. The mechanical testing of the sample before and after iodine doping was performed using an Instron equipment. In the undoped state, polyisoprene is a tacky and ductile solid with a relatively low modulus (~13 MPa). After doping, the samples become mechanically much stronger (modulus ~53 MPa). The doped sample was treated with a solvent such as hexane to extract the residual unreacted iodine. Then the film was observed to have the characteristic of a rubber band with excellent elastomeric property. Similar elastomeric property is also produced by doping with a controlled amount of iodine such that no residual unreacted iodine exists in the polymer. The doping has a similar effect as vulcanization along with strengthening using fillers.

Example 2

A styrene-butadiene-copolymer (SBR) sample in the form of latex was obtained from Goodyear Inc. Solid specimens of specific sizes and shapes were prepared by casting of the latex on a Teflon-coated aluminum substrate and by evaporation of the water. The samples were doped with iodine at different molar concentrations. The mechanical testing of the sample before and after iodine doping was performed using a Instron equipment. In the undoped state, SBR is a ductile solid with a relatively low modulus (~30 MPa). After doping, the samples become mechanically much stronger (modulus ~153 MPa). Removing the residual unreacted iodine with solvents such as hexane significantly enhanced the elastomeric property of the sample.

Example 3

A natural rubber (cis-1,4 polyisoprene) sample in the form of latex was obtained from Firestone Inc. Solid specimens of specific sizes and shapes were prepared by casting of the latex on a Teflon-coated aluminum substrate and by evaporation of the water. A mixture of sulfur and iodine with a higher content of sulfur was heated to form a dark material. This material was applied all around a rubber specimen. Then the sample was heated (~145° C.) for vulcanization. The time required for completion of vulcanization was found to be significantly shorter than using sulfur alone. The mechanical properties of this vulcanized sample were similar to that of rubber vulcanized with sulfur and carbon black. The presence of iodine in the vulcanized rubber acts as an insecticide.

The characteristics of the nonconjugated polymers and their advantages in the above applications are as follows:

1. Enhanced mechanical/elastomeric properties are obtained upon doping of nonconjugated polymers.
2. The elastic modulus in SBR increased about five times upon doping with iodine.
3. The elastic modulus of cis-1,4 polyisoprene (natural rubber) increased about four times upon doping with iodine.
4. The doping of natural rubber has a similar effect as vulcanization using sulfur along with strengthening with fillers.
5. The doping of SBR has a similar effect as vulcanization and strengthening with fillers.
6. The vulcanization of natural rubber with a heated mixture of sulfur and iodine leads to a faster rate of vulcanization compared to using sulfur alone.
7. Use of iodine along with sulfur in vulcanization overcomes the problem of insect-breeding (mosquitoes) on used tires.

Therefore, having thus described the invention, at least the following is claimed:

1. A process of vulcanization to enhance the mechanical properties of a nonconjugated conductive polymer by doping the polymer with iodine prior to vulcanization at at a temperature of ~145° C.

2. The process of claim 1, in which the nonconjugated polymer is cis-1,4 polyisoprene (natural rubber).

3. The process of claim 1 in which the vulcanized nonconjugated polymer is treated with a solvent to extract the unreacted iodine to enhance the elastomeric properties of the nonconjugated polymer.

4. The process of claim 3, in which the nonconjugated polymer is cis-1,4 polyisoprene.

5. A process of vulcanizing a nonconjugated polymer at a faster rate than the conventional process using sulfur alone, in which the nonconjugated polymer is vulcanized using a heated mixture of iodine and sulfur at a temperature of ~145° C.

6. The process of claim 5, in which the nonconjugated polymer is cis-1,4-polyisoprene (natural rubber).

7. A process of vulcanizing a nonconjugated polymer in latex form comprising evaporating a portion of the water from the latex, doping the latex with iodine and further evaporating the water until the latex is cured at a temperature of ~145° C.

8. The process of claim 7 in which sulfur is added to the iodine which is used to dope the latex.

9. A process of vulcanization to enhance the mechanical properties of a nonconjugated conductive polymer by doping the polymer with an electron acceptor prior to vulcanization at a of ~145° C.

10. The process of claim 9 in which the nonconjugated polymer is cis-1,4 polyisoprene (natural rubber).

11. The process of claim 9 in which the nonconjugated polymer is cis-1,4 polybutadiene.

12. The process of claim 9 in which the nonconjugated polymer is vulcanized using a heated mixture of an electron acceptor and sulfur.

* * * * *